(12) United States Patent
Manninen et al.

(10) Patent No.: US 11,337,733 B2
(45) Date of Patent: May 24, 2022

(54) DEROTATION APPARATUS FOR TREATING SPINAL IRREGULARITIES

(71) Applicant: GLOBUS MEDICAL, INC., Audubon, PA (US)

(72) Inventors: Katherine Manninen, Limerick, PA (US); Victoria Ferrari Alexander, Royersford, PA (US); Noah Hansell, King of Prussia, PA (US)

(73) Assignee: Globus Medical, Inc., Audubon, PA (US)

( * ) Notice: Subject to any disclaimer, the term of this patent is extended or adjusted under 35 U.S.C. 154(b) by 159 days.

(21) Appl. No.: 16/905,431

(22) Filed: Jun. 18, 2020

(65) Prior Publication Data

US 2020/0315663 A1 Oct. 8, 2020

Related U.S. Application Data

(60) Continuation of application No. 15/610,774, filed on Jun. 1, 2017, now Pat. No. 10,709,477, which is a continuation of application No. 14/643,537, filed on Mar. 10, 2015, now Pat. No. 9,693,806, which is a division of application No. 13/275,499, filed on Oct. 18, 2011, now Pat. No. 9,005,204, which is a continuation-in-part of application No. 12/632,445, filed on Dec. 7, 2009, now Pat. No. 8,475,467.

(51) Int. Cl.
*A61B 17/70* (2006.01)

(52) U.S. Cl.
CPC ...... *A61B 17/7001* (2013.01); *A61B 17/7037* (2013.01); *A61B 17/7041* (2013.01); *A61B 17/7079* (2013.01); *A61B 17/7086* (2013.01); *Y10S 606/914* (2013.01)

(58) Field of Classification Search
CPC ............ A61B 17/7086; A61B 17/7037; A61B 17/7001

See application file for complete search history.

(56) References Cited

U.S. PATENT DOCUMENTS

| 5,649,931 A | 7/1997 | Bryant et al. |
| 2004/0147937 A1 | 7/2004 | Dunbar |
| 2006/0271050 A1 | 11/2006 | Piza Vallespir |

(Continued)

FOREIGN PATENT DOCUMENTS

WO 2010065729 A2 6/2010

*Primary Examiner* — Olivia C Chang

(57) ABSTRACT

Treatment of spinal irregularities, including, in one or more embodiments, derotation apparatus and systems that can be used to reduce the rotation of vertebral bodies. Derotation apparatus that may comprise a tube assembly comprising an inner sleeve and an outer sleeve disposed over the inner sleeve. The inner sleeve may have a distal end for attachment to an implant. The tube assembly may further comprise a handle assembly. The tube assembly may further comprise a ball joint assembly disposed between the tube assembly and the handle assembly. The ball joint assembly may comprise a ball joint configured for attachment to a coupling rod. The ball joint assembly further may comprise a reducing extension below the ball joint, the reducing extension being sized to fit in a central bore of the inner sleeve. Orthopedic fixation devices comprising a ball joint are also disclosed.

20 Claims, 11 Drawing Sheets

(56) References Cited

U.S. PATENT DOCUMENTS

| | | | |
|---|---|---|---|
| 2007/0213715 A1* | 9/2007 | Bridwell | A61B 17/7032 |
| | | | 606/264 |
| 2007/0213716 A1* | 9/2007 | Lenke | A61B 17/7077 |
| | | | 606/264 |
| 2008/0015601 A1 | 1/2008 | Castro | |
| 2009/0228053 A1 | 9/2009 | Kolb | |
| 2011/0137358 A1 | 6/2011 | Manninen | |

* cited by examiner

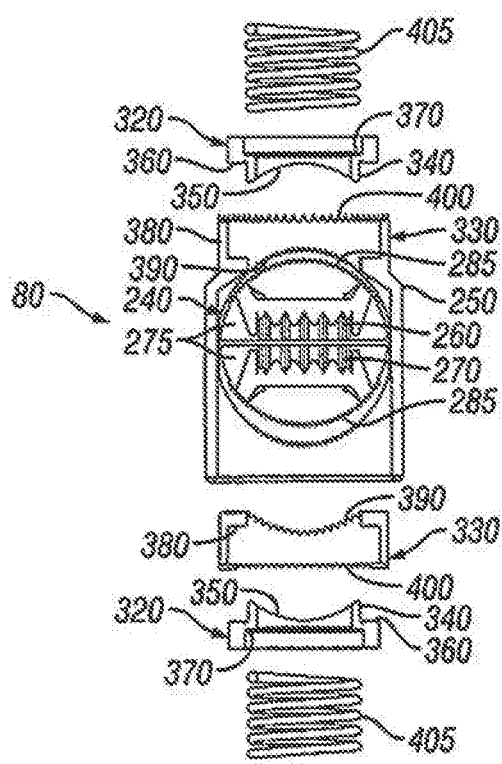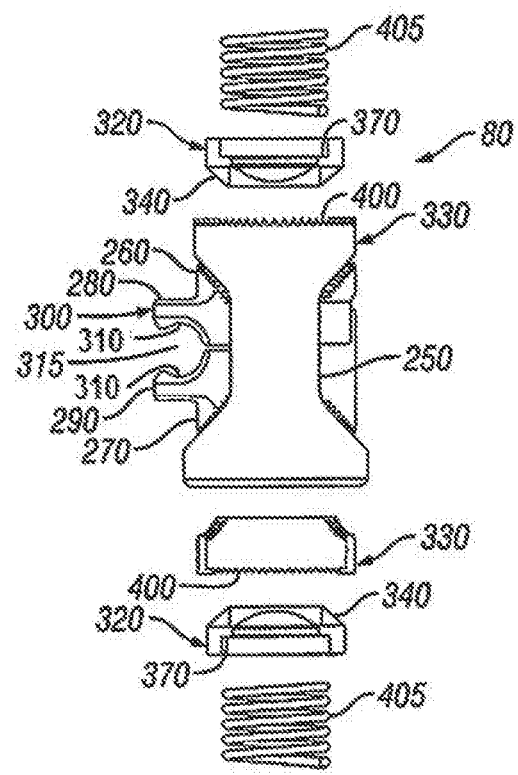
*FIG. 8*    *FIG. 9*
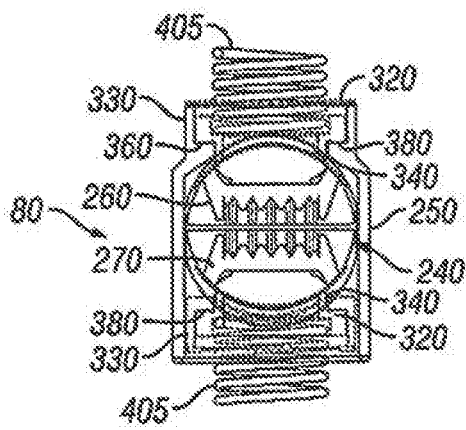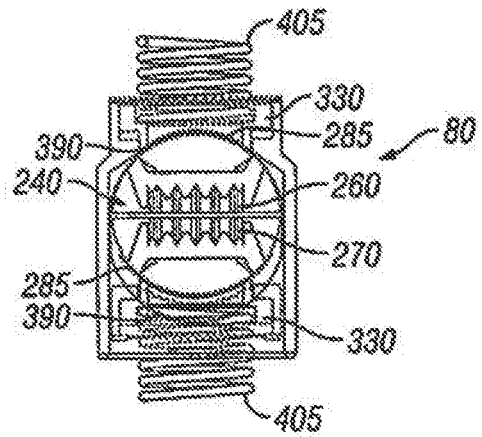
*FIG. 10*    *FIG. 11*

DEROTATION APPARATUS FOR TREATING SPINAL IRREGULARITIES

CROSS-REFERENCE TO RELATED APPLICATIONS

This application is a continuation of U.S. patent application Ser. No. 15/610,774, filed on Jun. 1, 2017 (published as U.S. Pat. Pub. No. 2017-0265899), which is a continuation of U.S. patent application Ser. No. 14/643,537, filed on Mar. 10, 2015, now U.S. Pat. No. 9,693,806, which is a divisional of U.S. patent application Ser. No. 13/275,499, filed on Oct. 18, 2011, now U.S. Pat. No. 9,005,204, which is a continuation-in-part of U.S. patent application Ser. No. 12/632,445, filed on Dec. 7, 2009, now U.S. Pat. No. 8,475,467, the entire disclosures of which are incorporated herein by reference in their entities for all purposes.

FIELD OF THE INVENTION

The present disclosure generally relates to treatment of spinal irregularities. In particular, in one or more embodiments, the present disclosure relates to derotation apparatus and systems that can be used to reduce the rotation of vertebral bodie.

BACKGROUND

Many types of spinal irregularities can cause pain, limit range of motion, or injure the nervous system within the spinal column. These irregularities can result from, without limitation, trauma, tumor, disc degeneration, and disease. By way of example, scoliosis and kyphosis are irregularities that can result in a complex, three-dimensional problem with lateral curvature of the spine and segmental vertebral rotation. Advances in medicine and engineering have provided doctors with a plurality of devices and techniques for correcting these deformities or irregularities.

One technique for treating scoliosis is the Harrington rod. The Harrington rod operates on a distraction system attached by hooks to the spine that when distracted, straightens the curve in the spine. Until the 1970's, the Harrington rod was the preferred method of treatment for scoliosis. Follow-up studies of these rods documented the negative effects of using distraction rods alone for correction of spinal deformities, including "flat back syndrome" and the resulting degenerative changes in the lower lumbar spine. Other methods of management, including spinal fixations systems that include segmental wires, hooks, rods and/or bone fasteners (e.g., pedicle screws) have revolutionized the treatment of spinal deformities. The advent and availability of smaller and stronger bone fasteners has further advanced treatment, allowing for effective application of corrective forces to posterior systems into the high thoracic spine.

Until recently, spinal fixation systems comprising bone fasteners and rods were used almost exclusively to correct the lateral curvature of the spine, with little attention paid to segmental vertebral derotation, primarily because bone fastener instrumentation did not provide a means of rotating the individual vertebral bodies. These systems focused on reducing the rod into the bone fasteners and using rod grips and/or in situ benders to translate the rod to restore sagittal and coronal plane balance. While these patients appear to be corrected on an A-P or lateral x-ray, they frequently present with pronounced rib hump, or axial twisting of the spine, which can result in significant pulmonary compromise and further degenerative changes in the spine.

Techniques have also been developed to address segmental vertebral rotation caused by irregularities, such as scoliosis. For instance, derotation systems have been used for the treatment of segmental vertebral rotation. Current derotation systems typically include a tube or series of tubes that slot over the implant (e.g., pedicle screw) much like a counter torque. These tubes allow the surgeon to push on and rotate the vertebral bodies away from the instrumentation, which when applied to the apex of the deformity, will straighten the lateral curvature and can reduce some of the individual rotation between bodies. However, this maneuver frequently results in flat back syndrome and, more importantly, very high applied forces to individual screws, which can lead to bone fasteners breaching the medial or lateral walls of the pedicle. This leads to loss of fixation at these levels and can result in paralysis if the breached screws impact the spinal cord. To reduce the force applied to any one screw, derotation systems may link multiple screws together so that the force of correction is applied over multiple screws. However, the surgeon typically cannot connect more than two tubes, and the process to connect the tubes is time consuming, confusing, and often requires separate instruments to assemble and tighten the system together. These factors in an already long and complex deformity case have limited the impact of derotation systems for posterior spinal fusion procedures.

Thus, there is a need for improved derotation systems that can securely connect to implants with efficient coupling to multiple implants.

SUMMARY

An embodiment of the present invention includes a derotation apparatus. The derotation apparatus may comprise a tube assembly comprising an inner sleeve and an outer sleeve disposed over the inner sleeve. The inner sleeve may have a distal end for attachment to an implant. The tube assembly may further comprise a handle assembly. The tube assembly may further comprise a ball joint assembly disposed between the tube assembly and the handle assembly. The ball joint assembly may comprise a ball joint configured for attachment to a coupling rod. The ball joint assembly further may comprise a reducing extension below the ball joint, the reducing extension being sized to fit in a central bore of the inner sleeve.

The features and advantages of the present invention will be readily apparent to those skilled in the art. While numerous changes may be made by those skilled in the art, such changes are within the spirit of the invention.

BRIEF DESCRIPTION OF THE DRAWINGS

FIG. 8 illustrates an exploded front view of a ball joint in accordance with one embodiment of the present invention.

FIG. 9 illustrates an exploded side view of a ball joint in accordance with one embodiment of the present invention.

FIG. 10 illustrates an embodiment of a ball joint in an unlocked position in accordance with one embodiment of the present invention.

FIG. 11 illustrates an embodiment of a ball joint in a locked position in accordance with one embodiment of the present invention.

DETAILED DESCRIPTION OF THE ILLUSTRATED EMBODIMENTS

Figure 1:
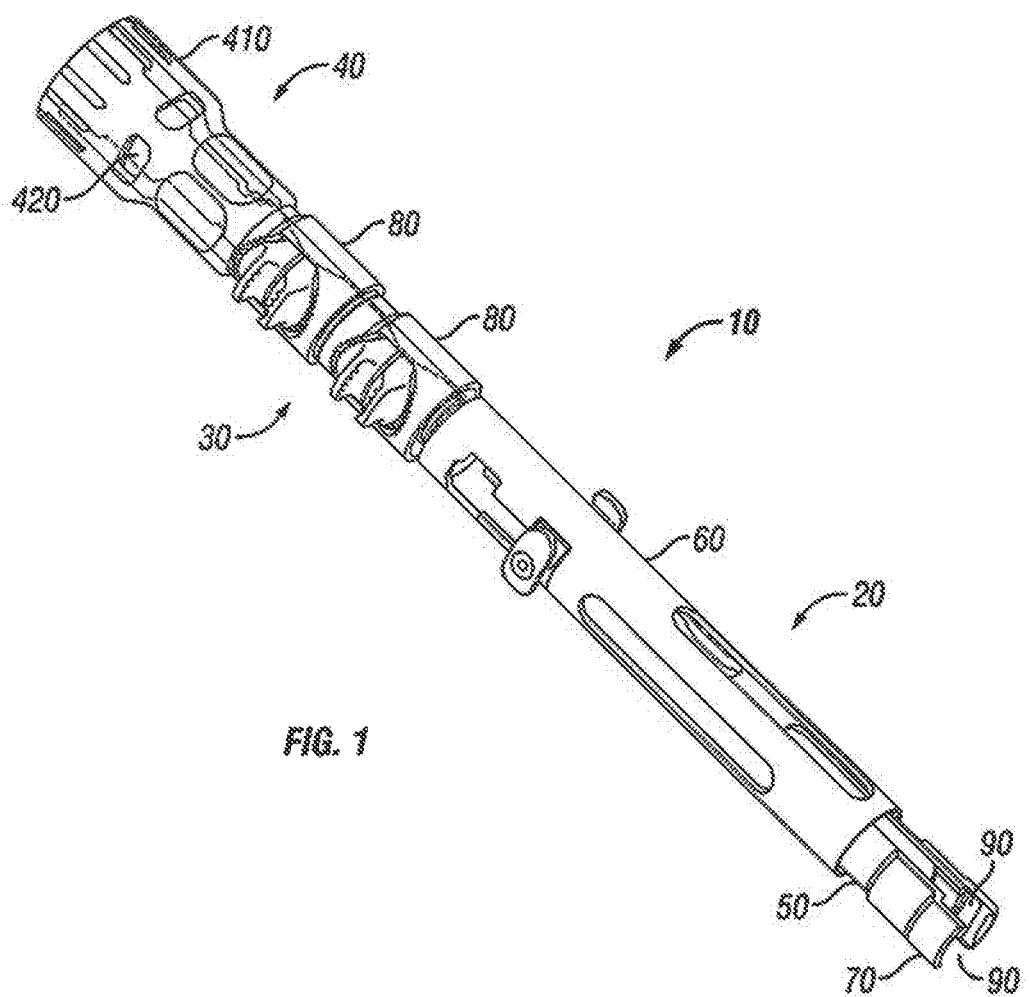
FIG. 1 illustrates a derotation apparatus in accordance with one embodiment of the present invention.
Figure 2:
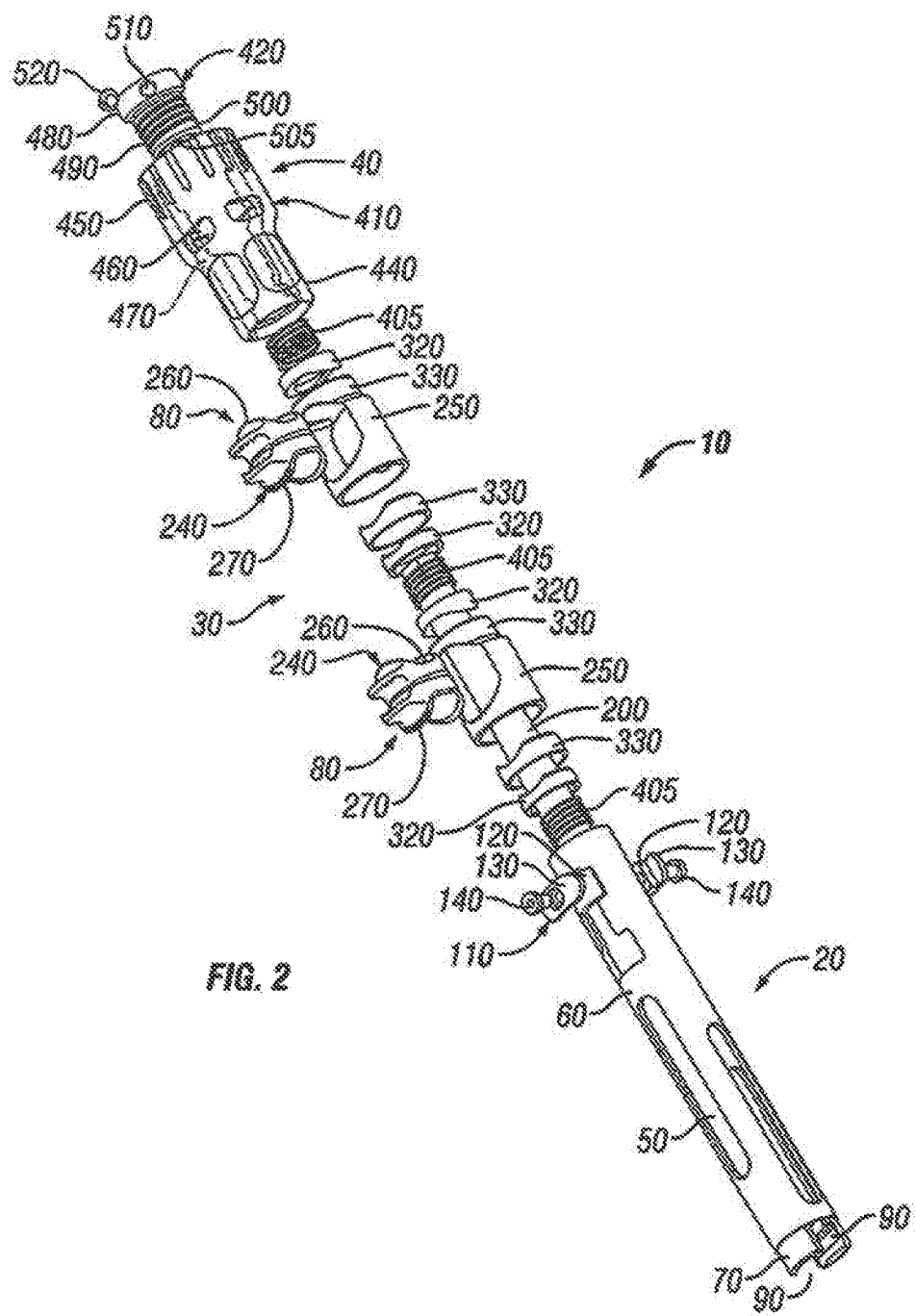
FIG. 2 illustrates an exploded view of a derotation apparatus in accordance with one embodiment of the present invention.

FIGS. 1 and 2 illustrate a derotation apparatus 10 in accordance with an embodiment of the present invention. As illustrated, derotation apparatus 10 comprises a tube assembly 20, a ball joint assembly 30, and a handle assembly 40. Tube assembly 20 may comprise an inner sleeve 50 and an outer sleeve 60 disposed over inner sleeve 50 with inner sleeve 50 having a distal end 70 configured and adapted for attachment to an implant (not illustrated). In an embodiment, the implant may be attached to a vertebral body. Ball joint assembly 30 may comprise at least one ball joint 80. As illustrated, ball joint assembly 30 comprises two ball joints 80. As will be discussed in more detail below, force may be applied to handle assembly 40 to derotate the vertebral body to which the implant is attached. This should result in reducing the rotation between vertebral bodies in a patient's spine. In addition, rotation of the vertebral bodies may also straighten curvature of the spine.

Figure 3:
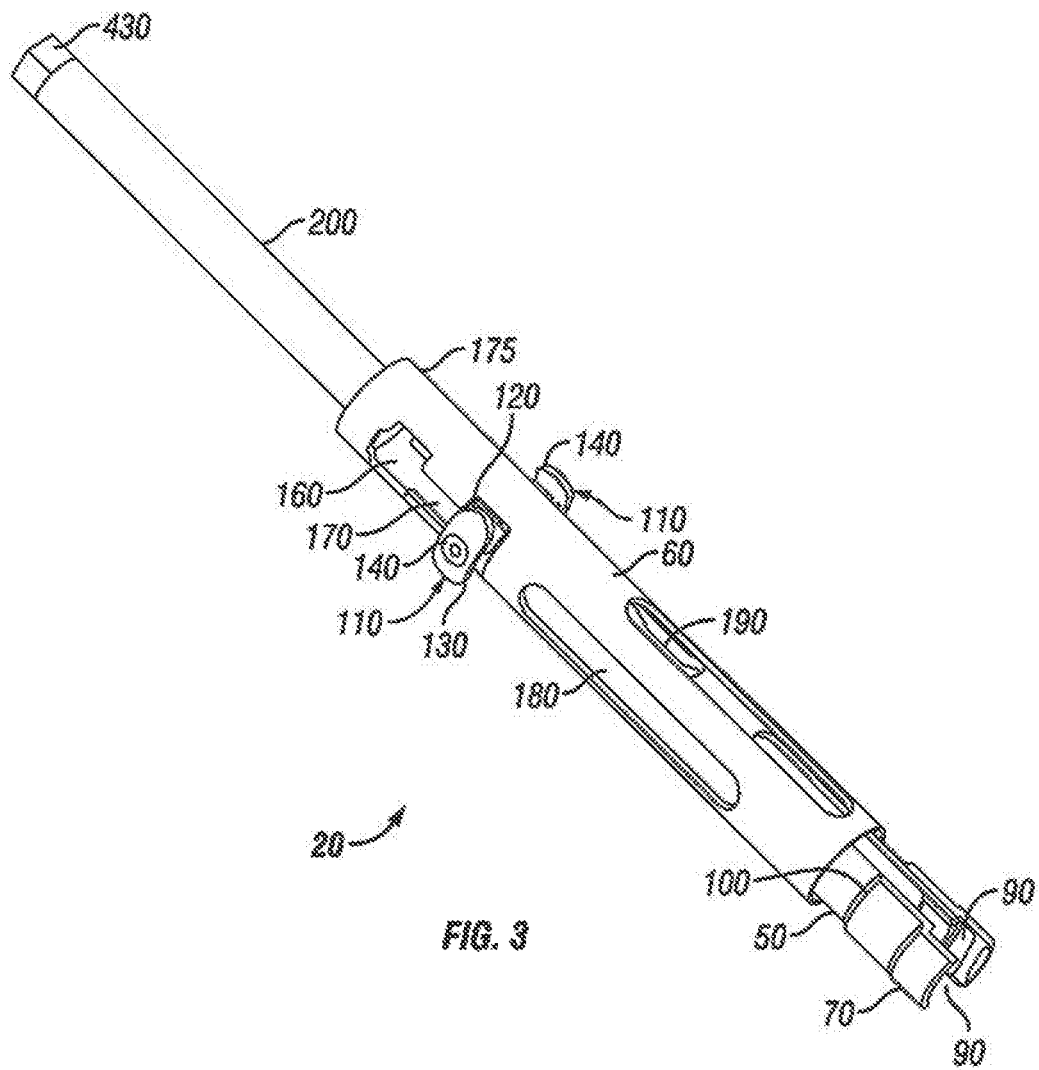
FIG. 3 illustrates an embodiment of a tube assembly of a derotation apparatus.

Referring now to FIGS. 1-5, tube assembly 20 of derotation apparatus 10 will be described in more detail in accordance with one embodiment of the present invention. FIG. 3 illustrates tube assembly 20 with ball joint assembly 30 and handle assembly 40 removed. In general, tube assembly 20 should attach derotation apparatus 10 to the implant (not illustrated). As previously mentioned, tube assembly 20 includes inner sleeve 50 and outer sleeve 60 disposed over inner sleeve 50.

Inner sleeve 50 includes distal end 70 configured and adapted for attachment to an implant (not illustrated). In an embodiment (not illustrated), distal end 70 fits over at least a portion of an implant. While not illustrated, the inner surfaces of distal end 70 may include features configured and adapted for attachment to the implant. For example, distal end 70 may include a connection that allows for coupling the inner sleeve 50 to the implant by applying some force. For example, the distal end 70 may be flexible so that the distal end 70 can fit over a head of the implant when longitudinal force is applied to the inner sleeve 50. In another embodiment, a dovetail-type connection may be included, such that placement of distal end 70 over the implant with rotation should couple the inner sleeve 50 to the implant, thus preventing separation. Other suitable mechanisms may be used to prevent separation of distal end 70 from the implant. The implant may include any of a variety of surgical implants that may be secured to a vertebral body, including, for example, a spine stabilization system that includes a bone fastener (e.g., a pedicle screw) coupled to a rod. By way of example, distal end 70 may fit over the head of the bone fastener. Distal end 70 may include slots 90 through which the rod extends when distal end 70 is fitted over the bone fastener, for example. Distal end 70 may further include a beveled surface 100.

Inner sleeve 50 may further include locking mechanisms 110 that extend radially from inner sleeve 50 opposite distal end 70. Locking mechanisms 110 may each include a stop 120, actuator 130, and guide 140. As illustrated, the stop 120 and actuator 130 may be on either end of the guide 140 with the guide 140, for example, being a pin or rod extending between stop 120 and actuator 130. Pressing down on actuator 130 should cause locking mechanisms 110 to depress towards inner sleeve 50.

Referring now to FIGS. 1-5, outer sleeve 60 will be described in more detail in accordance with one embodiment of the present invention. As previously mentioned, outer sleeve 60 may be disposed over inner sleeve 50. Outer sleeve 60 may comprise a first opening 150 and a second opening 160 connected by channel 170. While not illustrated, outer sleeve 60 further may comprise corresponding openings to first opening 150, second opening 160, and channel 170, on the opposite side of outer sleeve. First opening 150 and second opening 160 should each have a greater width than channel 170. Second opening 160 should be closer to proximal end 175 of outer sleeve 60 than first opening 150. Channel 170 should generally be dimensioned to allow passage of guide 140 of locking mechanisms 110, but should not be of sufficient size for passage of stop 120, when tube assembly 20 is assembled. First opening 150 and second opening 160 should be dimensioned to allow penetration of stop 120. Outer sleeve 60 further may comprise additional openings, such as third opening 180 and fourth opening 190. These additional openings should provide access to inner sleeve 50 after assembly of tube assembly 20, for example, so that interior components of tube assembly 20 may be inspected and/or cleaned as desired. In an embodiment, outer sleeve further comprises a chamfered distal end 210.

As illustrated by FIGS. 2 and 3, shaft 200 may be coupled to outer sleeve 60 in accordance with one embodiment of the present invention. In general, shaft 200 may extend axially from proximal end 175 of outer sleeve 60. In an embodiment, shaft 200 and outer sleeve 60 may be a unitary piece. In an alternative embodiment (not illustrated), shaft 200 may be attached to outer sleeve by any suitable mechanism, such as by a bolted and/or threaded connection. As illustrated, shaft may have a square-shaped proximal end 430. While proximal end 430 of shaft 200 is illustrated as generally square in shape other shapes (e.g., circular) may also be suitable in accordance with embodiments of the present invention.

Figure 4:
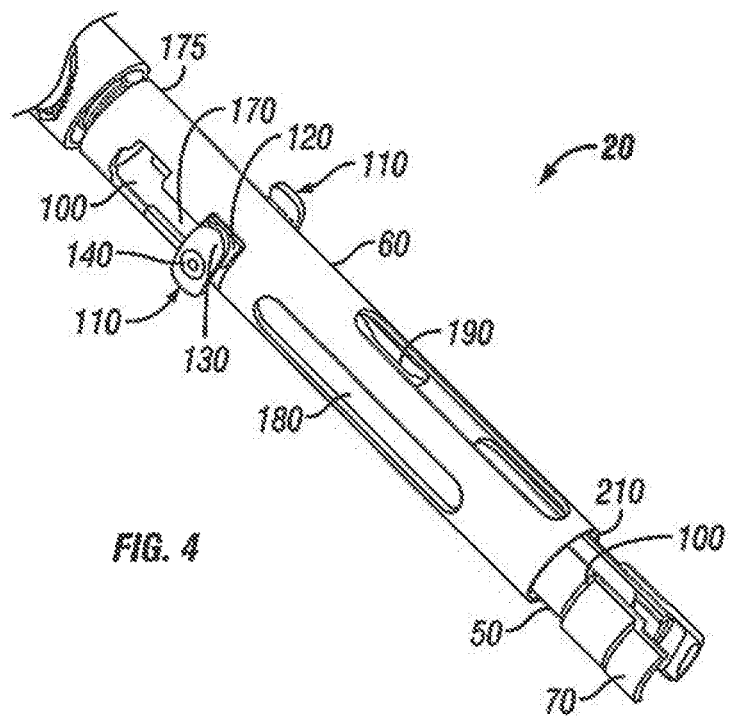
FIG. 4 illustrates an embodiment of a derotation apparatus with a tube assembly in an unlocked position.
Figure 5:
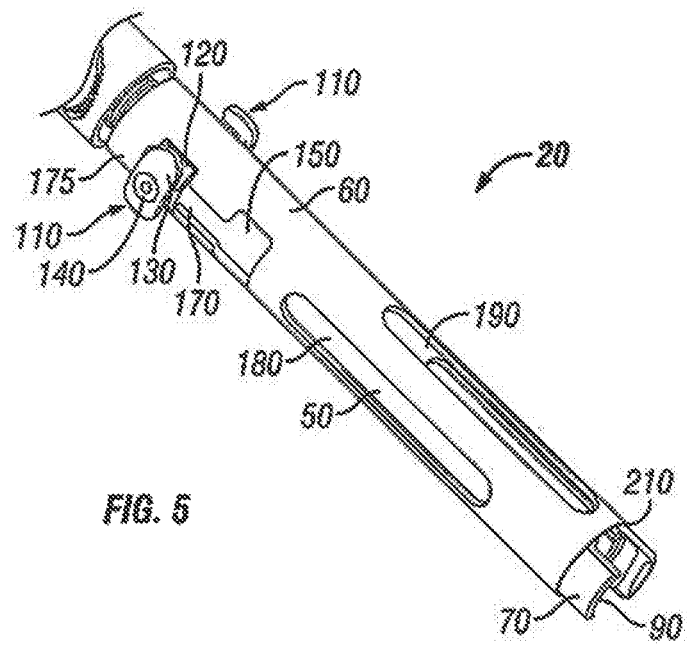
FIG. 5 illustrates an embodiment of a derotation apparatus with a tube assembly in a locked position in accordance with one embodiment of the present invention.

FIGS. 4 and 5 illustrate operation of the locking mechanisms 110 of tube assembly 20 in accordance with one embodiment of the present invention. As will be described below, locking mechanisms 110 may be used to couple derotation apparatus 10 to the implant (not illustrated). The following description is with respect to movement of one of locking mechanisms 110 from an unlocked to a locked position. However, it should be understood that the illustrated embodiment contains two locking mechanisms 110 with both locking mechanisms 110 functioning in a similar manner to effectuate locking and unlocking of tube assembly 20.

FIG. 4 illustrates tube assembly 20 with locking mechanism 110 in an unlocked position in accordance with one embodiment of the present invention. As illustrated, when tube assembly 20 is unlocked, outer sleeve 60 may be disposed over inner sleeve 50 with distal end 70 of inner sleeve 50 uncovered. In an embodiment, when unlocked, locking mechanism 110 should extend through first opening 150 in outer sleeve 60. Block 120 may be positioned in first opening 150 so that locking mechanism 110 is engaged with first opening 150, preventing movement of locking mechanism 110. This should fix the position of inner sleeve 50 with respect to outer sleeve 60. When in the unlocked position, distal end 70 of inner sleeve 50 may be placed over at least a portion of an implant (not illustrated). Various mechanisms may be applied so that the derotation apparatus 10 is prevented from separating from the distal end 70 of the implant.

FIG. 5 illustrates tube assembly 20 with locking mechanism 110 in a locked position in accordance with one embodiment of the present invention. The tube assembly 20 may be placed in the locked position to further secure the inner sleeve 50 onto the implant. To place the locking mechanism 110 in a locked position in accordance with one embodiment, actuator 130 should be pressed causing locking mechanism 110 to depress towards inner sleeve 50. Stop 120 may move completely through first opening 150 so that stop 120 disengages with first opening 150. With locking mechanism 110 depressed, pressure should be applied to tube assembly 20 forcing outer sleeve 60 further down onto inner sleeve 50. As outer sleeve 60 passes down onto inner sleeve 50, guide 140 should pass through channel 170 until locking mechanism 110 reaches second opening 160. Actuator 130 should then be released so that locking mechanism 110 raises and engages with second opening 160 with stop 120 preventing movement. As outer sleeve 60 is forced down onto first sleeve 50, chamfered distal end 210 of outer sleeve 60 passes over beveled surface 100. This forces the outer sleeve 60 against distal end 70 of inner sleeve 50 pressing distal end 70 tighter against the implant (not illustrated). This tightening force should clamp distal end 70 onto the implant preventing separation of distal end 70 from the implant. Accordingly, in this manner, derotation apparatus 10 can be securely connected to an implant. Other suitable mechanisms for securing derotation apparatus 10 onto an implant may also be used in accordance with embodiments of the present invention.

Figure 6:
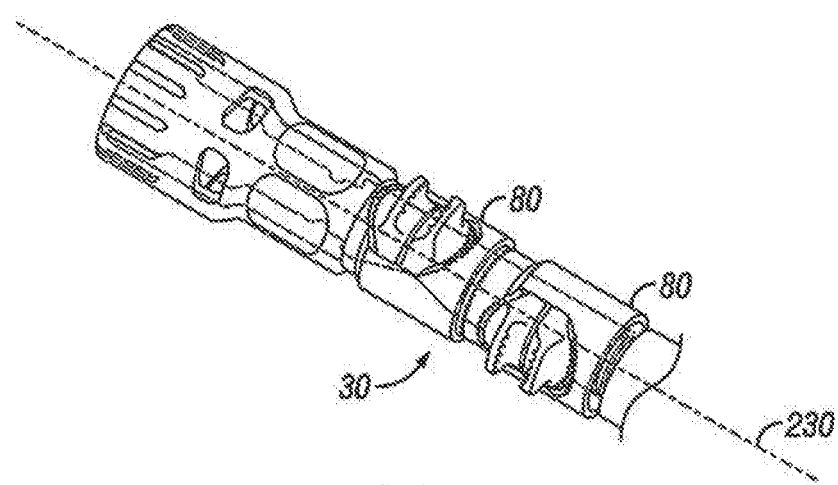
FIG. 6 illustrates an embodiment of a derotation apparatus with the ball joints at different rotational angles.
Figure 7:
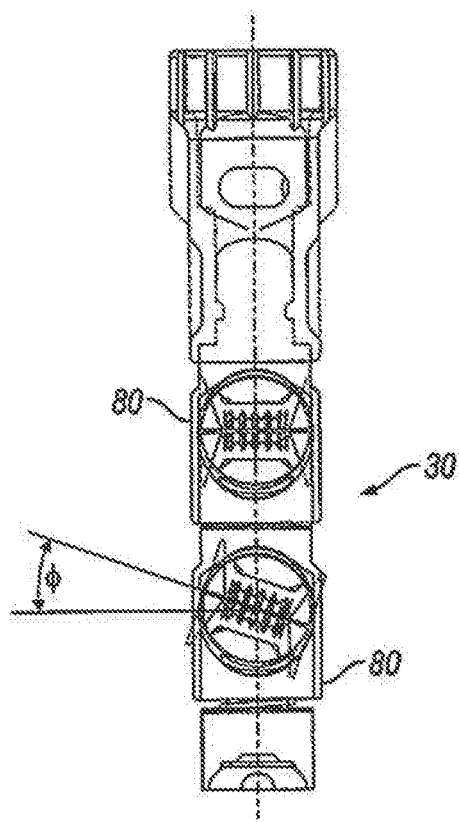
FIG. 7 illustrates an embodiment of a derotation apparatus with one of the ball joints oriented at an angled with respect to the derotation apparatus.

Derotation apparatus 10 may further comprise ball joint assembly 30. In general, ball joint assembly 30 should be configured and adapted to couple derotation apparatus 10 to least one additional derotation apparatus 10. As discussed below with respect to FIGS. 12-14, two or more derotation apparatuses 10 may be linked by at least one coupling rod 220 forming a coupled derotation system 225. Referring now to FIGS. 1 and 2, ball joint assembly 30 may comprise at least one ball joint 80. In an embodiment, at least one ball joint 80 may be a spring-loaded ball joint. In general, each of at least one ball joint 80 may be rotatable. For example, each of at least one ball joint 80 should be rotatable about at least one axis and, preferably, at least two axes. In an embodiment illustrated by FIG. 6, each of at least one ball joint 80 may be rotated about z-axis 230. For example, at least one ball joint 80 may rotate about z-axis 230 by an angle of up to about 360°. As illustrated, the two ball joints 80 may have an angle of rotation of about 90° with respect to one another. In an embodiment illustrated by FIG. 7, at least one ball joint 80 may be rotated about a y-axis (not illustrated), which would extend in a direction perpendicular to the figure. For example, at least one ball joint 80 may rotate about the y-axis by an angle ($\theta$) of up to about 360°. As illustrated, one of the ball joints 80 may rotate about the y-axis by an angle ($\theta$) of at least about 20°.

Referring now to FIGS. 2, 8 and 9, ball joint assembly 30 will be described in more detail with respect to one embodiment of the present invention. As illustrated, ball joint assembly 30 comprises at least one ball joint 80. Each ball joint 80 may comprise a ball 240 contained within a housing 250 with ball 240 and housing 250 disposed on shaft 200. In an embodiment, ball 240 is formed by upper portion 260 and lower portion 270 that when matched together form ball 240. Upper portion 260 and lower portion 270 may each be generally annularly shaped so that each portion can fit onto shaft 200. As illustrated, upper portion 260 may be a separate piece that forms the top half of ball 240 while lower portion 270 may be a separate piece that forms the lower half of ball 240. In an embodiment (not illustrated), upper portion 260 and lower portion 270 are unitary pieces or, alternatively, coupled in some manner. Each of upper portion 260 and lower portion 270 may comprise a hole, such as tapered through hole 275 to, for example, facilitate rotation of at least one ball joint 80 on shaft 200. In an embodiment, upper portion 260 and lower portion 270 of each ball joint 80 may comprise serrated ball edges 285 on at least a portion of their respective exterior surfaces forming the outer surface of respective ball 240.

In the illustrated embodiment, each of upper portion 260 and lower portion 270 comprises a tab, for example, upper tab 280 and lower tab 290. Upper tab 280 and lower tab 290 may extend radially and outwardly from upper portion 260 and lower portion 270, respectively. Together the upper tab 280 and lower tab 290 may be configured and adapted to form a clamp 300 that grips coupling rod 220 (illustrated on FIGS. 12-14). In this manner, each ball joint 80 may retain a corresponding coupling rod 220. In an embodiment, clamp 300 formed by upper tab 280 and lower tab 290 is open, for example, to facilitate insertion of coupling rod 220. In an embodiment, clamp 300 is generally u-shaped. As illustrated, the facing surfaces 310 of upper tab 280 and lower tab 290 may be rounded so that upper tab 280 and lower tab 290 form rod opening 315 for receiving coupling rod 220.

As illustrated by FIGS. 2, 8, and 9, each one ball joint 80 further may comprise inner washers 320 and outer washers 330 that are each disposed over shaft 200, in accordance with one embodiment of the present invention. Inner washers 320 and outer washers 330 may each comprise a central opening (not illustrated) that is dimensioned for shaft 200 to fit through. Inner washers 320 may each comprise a protruding rim 340 with a rounded surface 350. In an embodiment, rounded surface 350 may be smooth to allow for rotation of ball 240. Inner washers 320 also may each comprise an outer shoulder 360. As illustrated, outer shoulder 360 of each of inner washers 320 may be inwardly facing, in that outer shoulder 360 may face ball 240 of the respective ball joint 80. Inner washers 320 further may each comprise an inner spring shoulder 370 facing in the opposite direction of outer shoulder 360. Outer washers 330 may each comprise an inner shoulder 380. This inner shoulder 380 is outwardly facing because it faces away from ball 240. In an embodiment, one or more of outer washers 330 may be integral with housing 250. As illustrated by FIG. 8, this integral washer of outer washers 330 may be the uppermost of outer washers 330, in accordance with one embodiment. In an alternative embodiment (not illustrated), each of outer washers 330 may be separate pieces from housing 250. As illustrated by FIG. 9, the lowermost of outer washers 330 may be separate from housing 250 in accordance with one embodiment. In an embodiment, one or more of outer washers 330 may each comprise one or more serrated edges. In the illustrated embodiment, each of outer washers 330 may comprise inner serrated edge 390 and outer serrated edge 400. As illustrated, inner serrated edge 390 may be rounded for mating with ball 240.

Each ball joint 80 may further comprise springs 405. As illustrated, springs 405 may be disposed over shaft 200 on either side of inner washers 320. In an embodiment, springs 405 are compression springs. In an embodiment, each ball joint 80 may share one of springs 405. In the illustrated embodiment, each ball joint 80 comprises two springs 80 with each ball joint sharing one of springs 80. In an alternative embodiment (not illustrated), each of at least one ball joint 80 may comprise one compression spring.

Referring now to FIGS. 1 and 2, handle assembly 40 will be described in more detail, in accordance with one embodiment of the present invention. In the illustrated embodiment, handle assembly 40 comprises handle 410 and cap 420. Handle 410 may be generally tubular in shape with a passageway extending longitudinally therethrough. As illustrated, handle 410 may comprise lower tubular section 440 and upper tubular section 450. In an embodiment, lower tubular section 440 may have an inner diameter that is smaller than the inner diameter of upper tubular section 450. In an embodiment (not illustrated), lower tubular section 440 may have inner threads. When derotation apparatus 10 is assembled, shaft 200 may be received into lower tubular section 440. One or more holes 460 may be formed in upper tubular section 440. Handle 410 further may comprise inner cap shoulder 470, for example, at the intersection of lower tubular section 440 and upper tubular section 450. As illustrated, interior cap shoulder 470 may be upwardly facing.

In an embodiment, cap 420 may be configured and adapted to lock handle 410 on derotation apparatus 10. As illustrated, cap 420 may comprise head 480, elongated shaft 490, and exterior threads 500. When derotation apparatus 10 is assembled, for example, cap 420 may be disposed in the interior of handle 410 with cap 420 engaging inner cap shoulder 470 of handle 410 and elongated shaft 490 extending down into lower tubular section 440. While not illustrated, cap 420 may include features to lock into handle 410. In an embodiment (not illustrated), cap 420 may be threaded into lower tubular section 440 of handle 410. For example, exterior threads 500 of cap 420 may thread into interior threads (not illustrated) in lower tubular section 440. In addition, cap 420 may also include features to secure handle 410 and ball joint assembly 30 on shaft 200. For example, cap 420 may be disposed over proximal end 430 of shaft 200 with screw 520 inserted into threaded hole 510 of cap 420 to engage shaft 200. As illustrated, threaded hole 510 may be in head 480 of cap 420. In an embodiment, elongated shaft 490 may have a rectangular shaped opening 505 into which square-shaped proximal end 430 of shaft 200 may be inserted. It should be understood that other shaped openings in elongated shaft 490 may also be suitable for use in embodiments of the present invention. With cap 420 secured onto shaft 200, handle 410 may be rotated to, for example, tighten handle 410 down onto shaft 200, thus tightening handle 410 down onto ball joint assembly 30. The preceding description describes handle assembly 40 that can be used in accordance with an embodiment of the present invention. However, it should be understood that other suitable assemblies for tightening down onto ball joint assembly 30 can be used in accordance with embodiments of the present invention.

Referring now to FIG. 10, ball joint 80 is illustrated in an unlocked position in accordance with one embodiment of the present invention. As illustrated, outer washers 330 may be located on either side of ball 240. As previously described, ball 240 may be formed by upper portion 260 and lower portion 270 that match together to form ball 240. In the illustrated embodiment, the uppermost of outer washers 330 is integral with housing 250 with the lowermost of outer washers 330 slidably disposed within housing 250. Inner washers 320 may also be located on either side of ball 240. Outer shoulder 360 of each of inner washers 320 should engage corresponding inner shoulder 380 of outer washers 330. As illustrated, protruding rim 340 of each of inner washers 320 may extend through a corresponding one of outer washers 330. Rounded surface 350 of protruding rim 340 of each of inner washers 320 may contact ball 240. As previously mentioned, rounded surface 350 may be smooth to allow for rotation of ball 240. As illustrated, springs 405 may be located on either side of inner washers 320. In the illustrated embodiment, springs 405 engage inner spring shoulder 370 of inner washers 320. In an embodiment, springs 405 may force outer shoulder 360 of each inner washer 320 into engagement with inner shoulder 380 of each outer washer 330.

Referring now to FIG. 11, ball joint 80 is illustrated in a locked position in accordance with one embodiment of the present invention. Ball joint 80 may be placed in a locked position to secure coupling rod 220 in clamp 300 (illustrated on FIGS. 12-14). To place ball joint 80 in a locked position in accordance with one embodiment, handle assembly 40 may be tightened down onto ball joint assembly 30, for example. As the handle assembly 40 is tightened, inner washers 320 may be pushed inside of outer washers 330 so that protruding rim 340 no longer extends through outer washers 330. The outer washers 330 may then engage ball 240 with springs 405 forcing upper portion 260 and lower portion 270 together. By forcing upper portion 260 and lower portion 270 together, clamp 300 may be closed onto a coupling rod 220 (illustrated on FIGS. 12-14). In addition, engagement of outer washers 330 with ball 240 may also prevent rotation of ball 240. As previously mentioned, outer washers 330 and/or outer surfaces 240 of ball 240 may be serrated. In an embodiment, inner serrated edge 390 of each outer washer 330 engages serrated ball edges 285 to prevent rotation of ball 240. The preceding description describes one suitable technique for locking ball joint 80 to prevent rotation of ball 240 and secure coupling rod 220 in clamp 300. However, it should be understood that other suitable techniques for preventing rotation of ball 240 and for securing coupling rod 220 in clamp 300 can be used in accordance with embodiments of the present invention.

One or more derotation apparatuses 10 may be used in the treatment of spinal irregularities in accordance with embodiments of the present invention. For example, derotation apparatus 10 may be used to derotate a vertebral body, thus reducing rotation between vertebral bodies in a patient's spine. Derotation of the vertebral body with derotation apparatus 10 may also straighten curvature of the spine. In an embodiment, derotation apparatus 10 may be used in conjunction with an implant (e.g., a bone fastener coupled to a rod) to also address curvature of the spine. An embodiment of treating a spinal irregularity may include coupling derotation apparatus 10 to an implant. In an embodiment, the implant may be attached to a vertebral body. Coupling derotation apparatus 10 to an implant may include, for example, placement of distal end 70 of inner sleeve 50 over implant. In an embodiment, distal end 70 may be placed over implant to prevent separation of inner sleeve from implant. Coupling derotation apparatus 10 to implant further may include placing tube assembly 20 into a locked position to further secure inner sleeve 50 onto implant. In an embodiment, in the locked position, outer sleeve 60 may be disposed over distal end 70 of inner sleeve 50, clamping distal end 70 onto the implant. After securing the inner sleeve 50 on the implant, force may be applied to handle assembly 40 to derotate the vertebral body to which the implant is attached.

Embodiments for treating a spinal irregularity further may include coupling derotation apparatus 10 to at least one additional derotation apparatus 10 to form a coupled derotation system 225. For example, ball joints 80 in separate derotation apparatus 10 may be aligned so that a coupling rod 220 may be placed into a corresponding clamp 300 of the aligned ball joints 80. To lock the coupling rod 220 in place, the aligned ball joints 80 may then be placed in a locked position, for example, by tightening of a corresponding handle assembly 40. It should be understood that each derotation apparatus 10 in coupled derotation system 225 may be coupled to a corresponding implant. Force may be applied to handle assembly 40 in at least one derotation apparatus 10 in coupled derotation system 225. In an embodiment, force may be applied to handle assembly 40 of each derotation apparatus 10 in coupled derotation system 225. Application of force to handle assembly 40 should derotate the vertebral bodies to which coupled derotation system 225 is attached.

Figure 12:
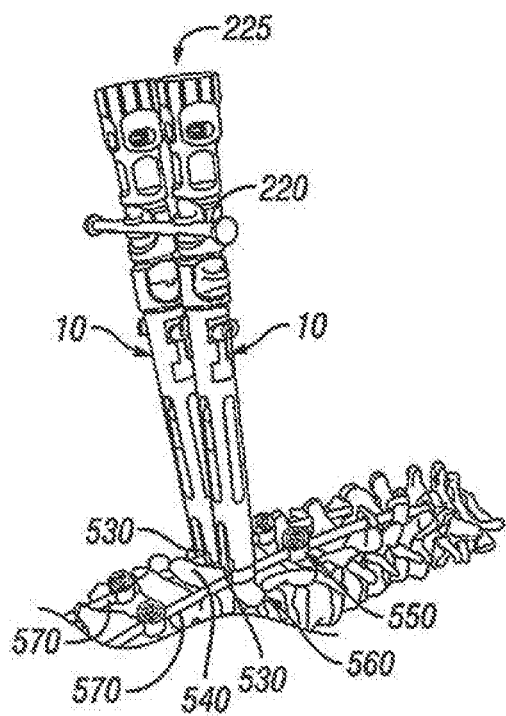
FIG. 12 illustrates an embodiment of a coupled derotation system with two derotation apparatuses attached on either side of the same vertebral body.

Referring now to FIG. 12, coupled derotation system 225 for treatment of spinal irregularities is illustrated in accordance with one embodiment of the present invention. As illustrated, coupled derotation system 225 includes two derotation apparatuses 10 interconnected by coupling rod 220. In the illustrated embodiment, derotation apparatuses 10 are connected to bone fasteners 530 on either side of vertebral body 540. Rotational force applied to vertebral body 540 should be distributed between bone fasteners 530. As illustrated, bone fasteners 530 may be a component of a bone fixation system 550 for fusing spine 560 that may include a single rod or a pair of parallel rods 570.

Figure 13:
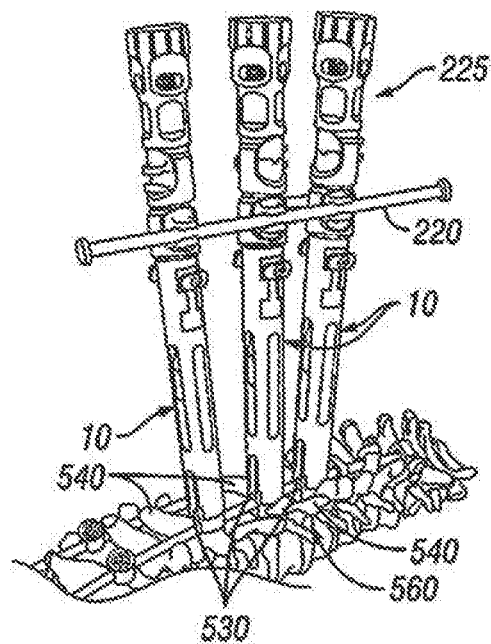
FIG. 13 illustrates an embodiment of a coupled derotation system with three derotation apparatuses in an inline arrangement.

Referring now to FIG. 13, an embodiment of coupled derotation system 225 for treatment of spinal irregularities is illustrated in which three derotation apparatuses 10 interconnected by coupling rod 220 are connected to bone fasteners 530 on the same side of spine 560. In an embodiment, derotation apparatuses 10 may be connected to vertebral bodies 540 at the apex of the curvature of spine 560. This arrangement of derotation apparatuses 10 should distribute force across multiple levels of spine 560.

Figure 14:
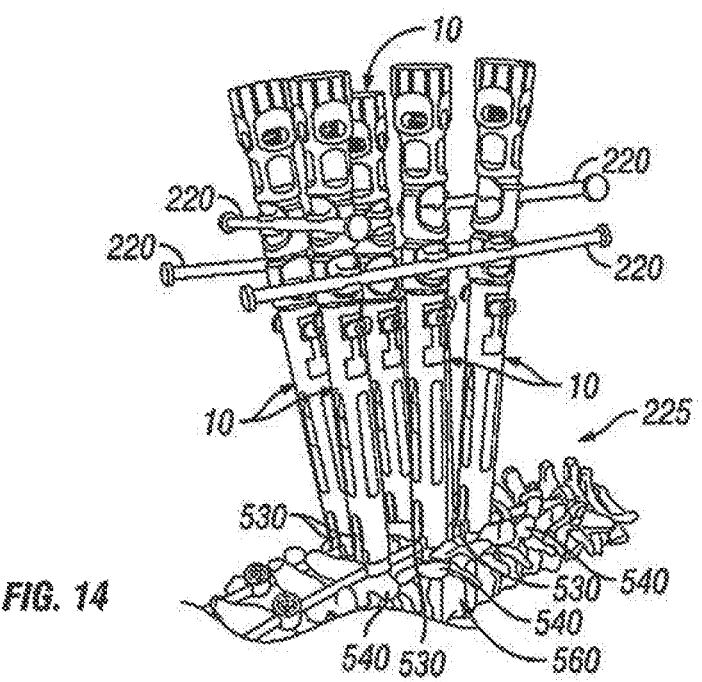
FIG. 14 illustrates an embodiment of a coupled derotation system with multiple derotation apparatuses.

Referring now to FIG. 14, an embodiment of coupled derotation system 225 for treatment of spinal irregularities is illustrated in which multiple derotation apparatuses 10 are interconnected by coupling rods 220. As illustrated, derotation apparatuses 10 may be coupled to bone fasteners 530 over multiple levels of spine 560 and on both sides of spine 560. This arrangement of derotation apparatuses 10 should distribute force across multiple levels of spine 560 for derotation of vertebral bodies 540.

Figure 15:
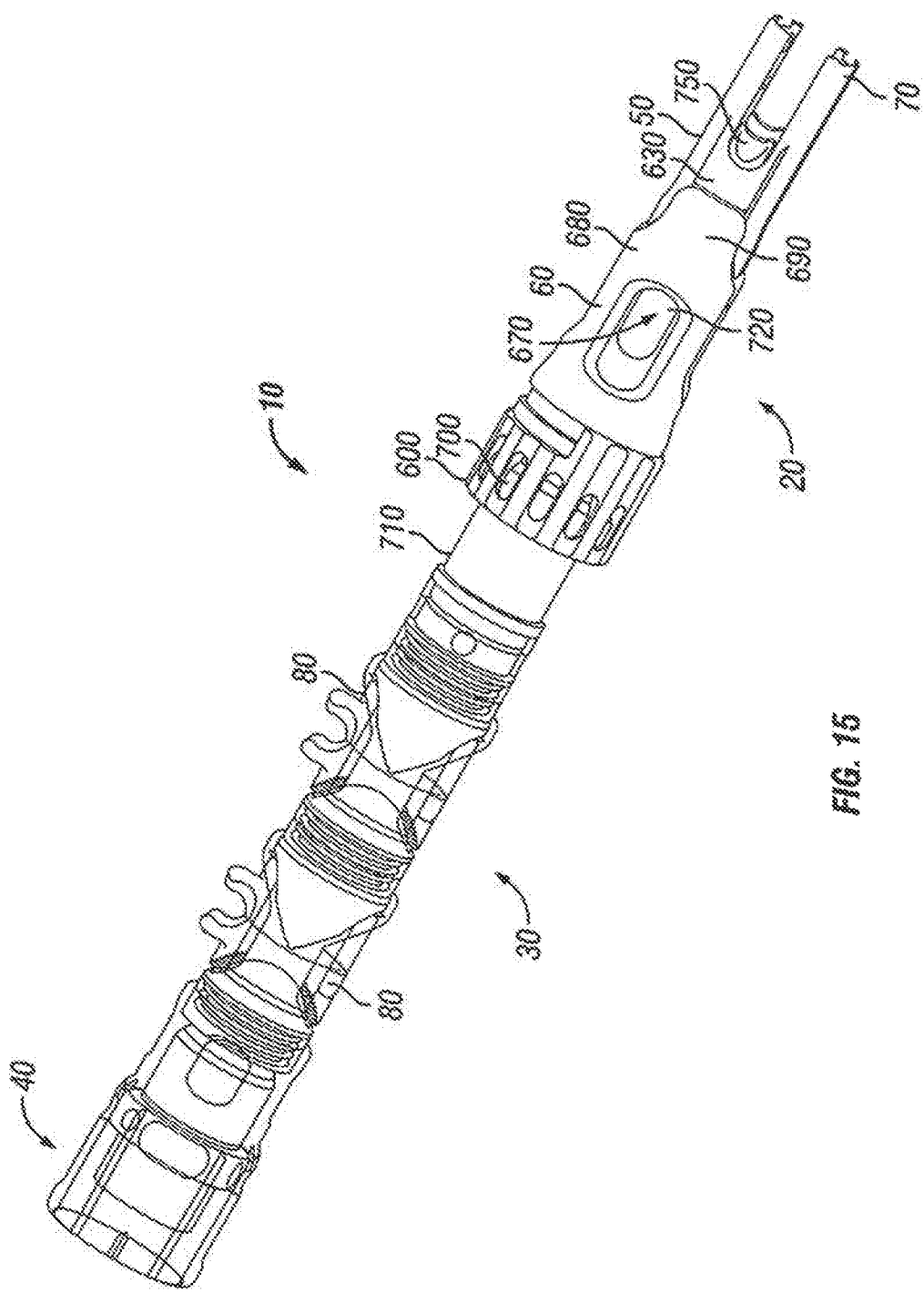
FIG. 15 illustrates a derotation apparatus in accordance with alternative embodiments of the present invention.

FIG. 15 illustrates a derotation apparatus 10 in accordance with alternative embodiments of the present invention. As illustrated, derotation apparatus 10 includes a tube assembly 20, a ball joint assembly 30, and a handle assembly 40.

Figure 16:
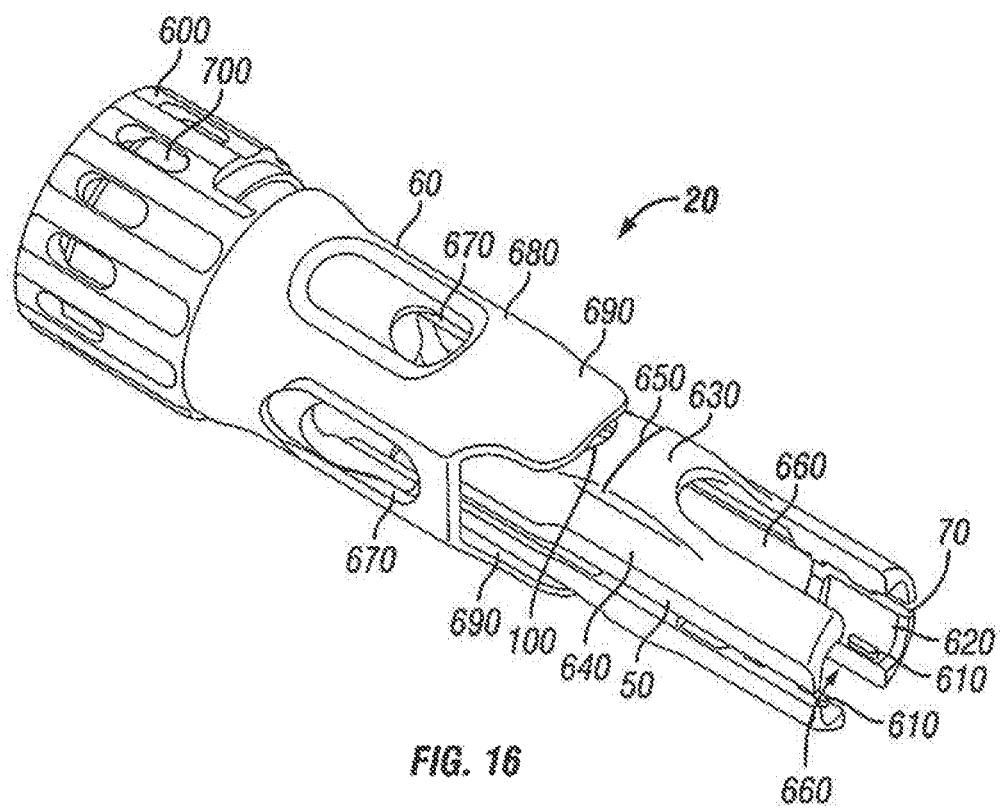
FIG. 16 illustrates an embodiment of a tube assembly of the derotation apparatus of FIG. 15.
Figure 17:
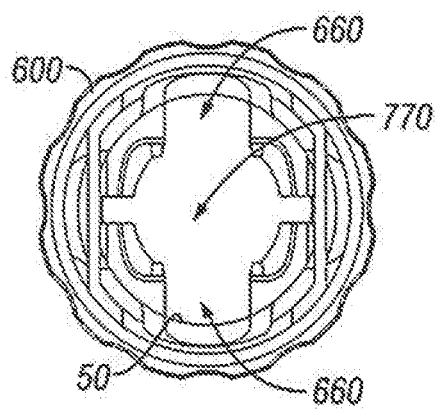
FIG. 17 illustrates an end view of the tube assembly of FIG. 16 in accordance with one embodiment of the present invention.

With reference to FIGS. 15-17, tube assembly 20 of derotation apparatus 10 of FIG. 15 will be described in more detail in accordance with embodiments of the present invention. As illustrated, tube assembly 20 may include an inner sleeve 50, an outer sleeve 60, and a locking handle 600. In the illustrated embodiment, inner sleeve 50 has a distal end 70 configured and adapted for attachment to an implant (not illustrated). Embodiments for attaching distal end 70 to the implant are described in more detail above with respect to FIGS. 1-5. For example, distal end 70 may be flexible so that distal end 70 can be pushed onto the head of a bone fastening device (e.g., a pedicle screw). As best seen in FIG. 16, distal end 70 further may include features 610 on an inner surface 620 of distal end 70 for allowing distal end 70 to slot onto the implant. In the illustrated embodiment, the features 610 are illustrated as protruding from interior surface 620. Inner sleeve 50 further may include at least one protruding surface 630, which may include beveled surface 100, for example. In the illustrated embodiment, protruding surface 630 extends outward from exterior surface 640 of inner sleeve 50. As illustrated, protruding surface 630 further may include raised stop 650 on the surface thereof. Inner sleeve 50 further may include longitudinally extending slots 660.

As illustrated by FIGS. 15 and 16, outer sleeve 60 may be disposed over inner sleeve 50 for locking inner sleeve 50 onto an implant. Outer sleeve 60 may comprise one or more openings 670. These openings 670 should provide access to inner sleeve 50, for example, so that interior components of the tube assembly 20 may be inspected and/or cleaned as desired. In the illustrated embodiment, distal end 680 of outer sleeve 60 includes one or more tabs 690 that extend longitudinally from outer sleeve 60.

As previously mentioned, tube assembly 20 further may include locking handle 600. As illustrated by FIGS. 15-17, locking handle 600 may be disposed on a proximal end 700 of inner sleeve 50. While not illustrated, locking handle 600 may be threadedly connected to proximal end 700 of inner sleeve 50, for example. The locking handle 600 may be configured to rotate and move down inner sleeve 50 placing the tube assembly 20 in a locked position, thus coupling the derotation apparatus 10 to an implant in accordance with embodiments of the present invention. As locking handle 600 is turned and moves down inner sleeve 50, locking handle 600 should engage outer sleeve 60 causing outer sleeve 60 to translate distally. As outer sleeve 60 translates distally, the tabs 690 of outer sleeve 60 should engage at least one protruding surface 630 on inner sleeve 50 such that distal end 70 of inner sleeve 50 is pressed tighter against the implant (not illustrated), for example. This tightening force should clamp distal end 70 onto the implant preventing separation of distal end 70 from the implant. Accordingly, in this manner, derotation apparatus 10 can be securely connected to an implant. Other suitable mechanisms for securing derotation apparatus 10 onto an implant may also be used in accordance with embodiments of the present invention.

Figure 18:
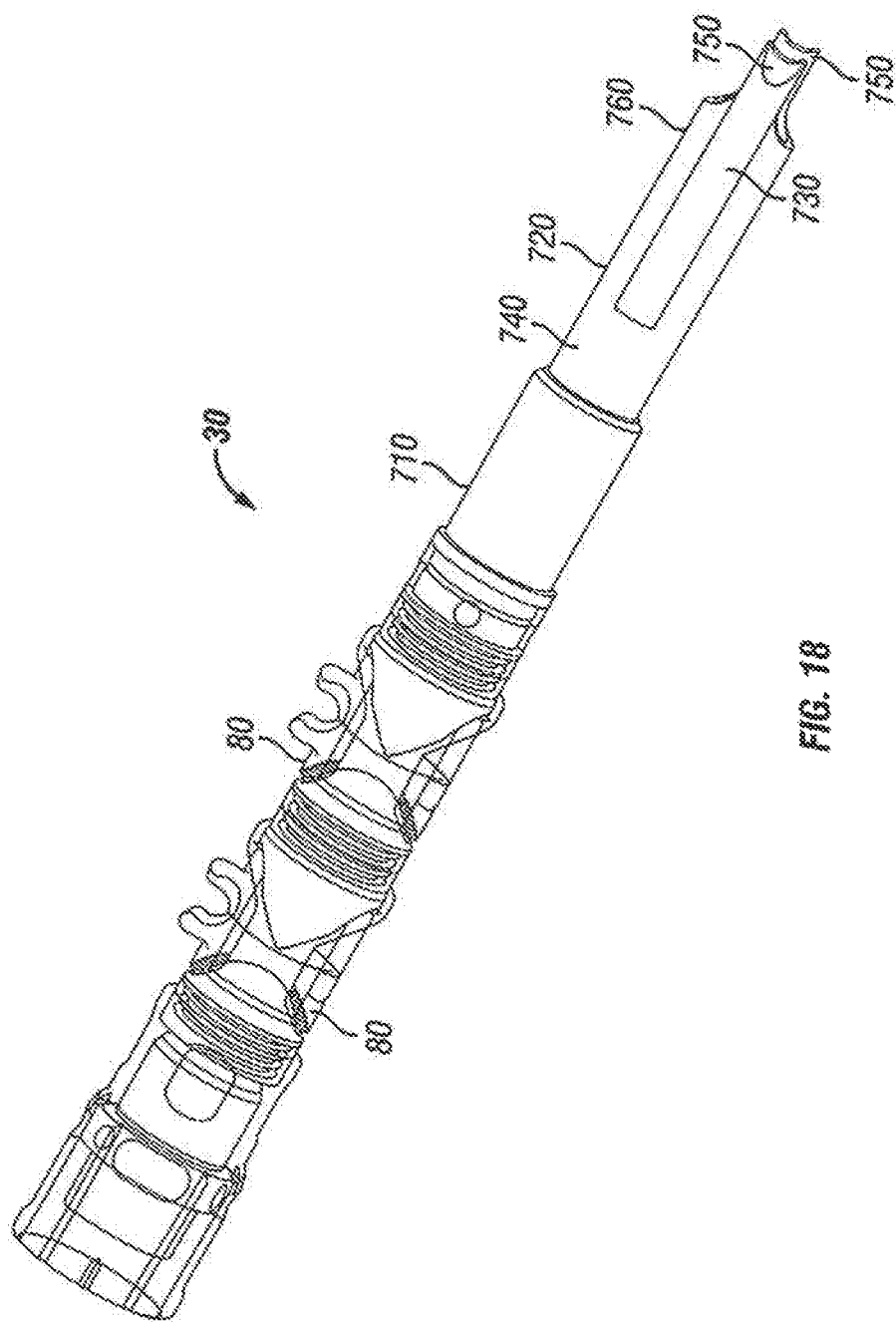
FIG. 18 illustrates an embodiment of a ball joint assembly with a handle assembly disposed at one end of the ball joint assembly, the ball joint assembly having a reducing extension.

Derotation apparatus 10 of FIG. 15 further includes ball joint assembly 30 in accordance with embodiments of the present invention. In general, ball joint assembly 30 should be configured and adapted to couple derotation apparatus 10 to at least one additional derotation apparatus 10. With reference to FIGS. 15 and 18, ball joint assembly 30 includes one or more ball joints 80. Embodiments for operating ball joints 80 to secure a rod 220 (e.g., FIG. 12) are described in more detail above with respect to FIGS. 1, 2, and 6-11. As best seen by FIG. 18, ball joint assembly 30 further may include tube 710 below ball joints 80 with tube 710 including reducing extension 720. As illustrated, reducing extension 720 may have a reduced diameter as compared to tube 710. Reducing extension 720 further includes one or more raised surfaces 730 projecting from exterior surface 740 of reducing extension 720. In the illustrated embodiment, reducing extension 720 includes two raised surfaces 730 on either side of reducing extension 720. In some embodiments, the raised surfaces 730 may extend longitudinally at least partially the length of reducing extension 720. As illustrated, each of the raised surfaces 730 include reducer tabs 750 that project beyond distal end 760 of reducing extension 720. Reducing extension 710 may be sized to fit in central bore 770 (e.g., FIG. 17) of inner sleeve 50. Raised surface 730 may be sized and configured to fit into longitudinally extending slots 660 (e.g., FIG. 17) in inner sleeve 50 to key the ball joint assembly 30 and sleeve assembly 20 so that the components are properly oriented. Ball joint assembly 30 may be coupled to sleeve assembly 20. By way of example, ball joint assembly 30 may be coupled to sleeve assembly 20 by a threaded connection. While not illustrated, a portion of ball joint assembly 30, such as an exterior surface of tube 710, may have threads that engage corresponding threads in proximal end 700 of inner sleeve 50. Threading the ball joint assembly 30 into sleeve assembly 20, for example, should distally translate reducer tabs 750. In accordance with present embodiments, distal translation of reducer tabs 750 can be used to reduce a rod 570 (e.g., FIG. 12) into the head of a bone fastener 530 (e.g., FIG. 12), such as a screw, to which the sleeve assembly 20 is attached.

Derotation apparatus of FIG. 15 further includes handle assembly 40 in accordance with embodiments of the present invention. Use of the handle assembly 40 to, for example, tighten the ball joints 80 onto a rod 220 (e.g., FIG. 12) is described in more detail above with respect to FIG. 1.

While the preceding description describes the use of one or more ball joints 80 (e.g., FIG. 1) in a derotation apparatus 10, it should be understood that ball joints 80 may be used for securing rods or other members (e.g., an artificial facet) to other medical devices. By way of example, one or more ball joints 80 may be used with an orthopedic fixation device 800, as described below with respect to FIGS. 19-20. In one embodiment, orthopedic fixation device 800 is a pedicle screw.

Figure 19:
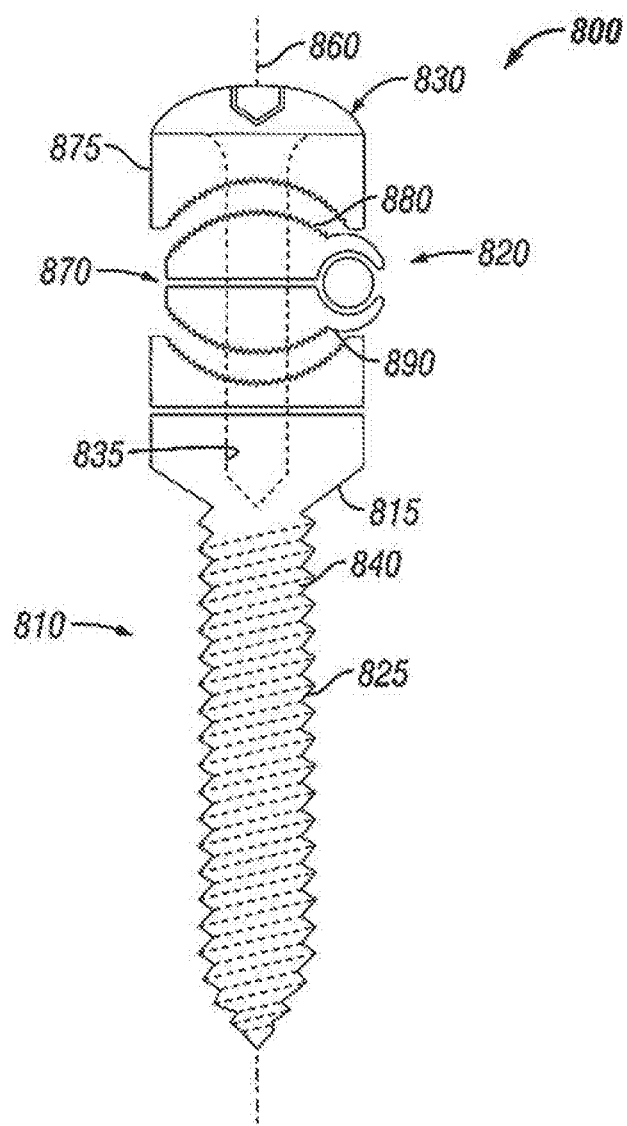
FIG. 19 illustrates an orthopedic fixation device in accordance with one embodiment of the present invention.

FIG. 19 illustrates an orthopedic fixation device 800 comprising a bone fastener 810, an offset rod connection assembly 820, and a locking cap assembly 830. In the illustrated embodiment, bone fastener 810 includes head 815 and shaft 825. The illustrated embodiment shows shaft 825 having threads 840. In some embodiments (not illustrated), shaft 825 may have a tapered shape. Those of ordinary skill in the art will appreciate that shaft 825 may have a number of different features, such as thread pitch, shaft diameter to thread diameter, overall shaft shape, and the like, depending, for example, on the particular application. As illustrated, the shaft 825 extends downwardly from head 815. In certain embodiments, head 815 may have a tool engagement surface, for example, that can be engaged by a screw-driving tool or other device. The tool engagement surface can permit the physician to apply torsional or axial forces to bone fastener 810 to drive bone fastener 810 into bone, for example. In the illustrated embodiment, the tool engagement surface of head 815 is a recess 835. For instance, recess 835 may be polygonal (e.g., hexagonal) for receiving a polygonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

Figure 20:
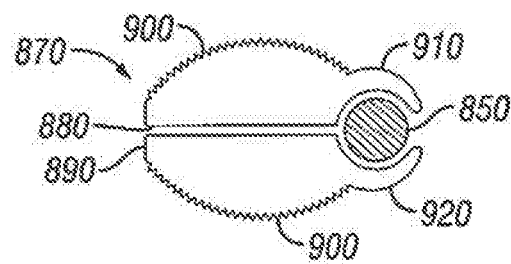
FIG. 20 illustrates coupling of a ball joint of the orthopedic fixation device of FIG. 19 to a rod in accordance with one embodiment of the present invention.

With additional reference to FIG. 20, offset rod connection assembly 820 is configured to secure a rod 850 offset from longitudinal axis 860 of orthopedic fixation device 800 in accordance with embodiments of the present invention. Alternatively, the connection assembly 820 may be used to secure another member, such as an artificial facet, instead of rod 850. Moreover, connection assembly 820 may be configured to rotate polyaxially so that rod 850 can be placed in a desired position with respect to shaft 810. In some embodiments, offset rod connection assembly 820 may be a ball joint (e.g., ball joint 80 on FIG. 1). Embodiments of offset rod connection assembly 820 may operate to clamp onto rod 850 in manner similar to that described previously for ball joint 80. For example, offset rod connection assembly 820 may be rotatable about at least one axis and, preferably, at least two axes. For example, connection assembly 820 may be configured to rotate about at least one, or both, of the y-axis and z-axis. As illustrated, offset connection assembly 820 may comprise a ball 870 contained within housing 875. In one embodiment, ball 870 is formed by upper portion 880 and lower portion 890 that when matched form ball 870. In an embodiment, upper portion 880 and lower portion 890 of ball 870 may each comprise serrated ball edges 900 on at least a portion of their respective exterior surfaces forming the outer surface of ball 870, as best seen on FIG. 20. In the illustrated embodiment, each of upper portion 880 and lower portion 890 comprises a tab, for example, upper tab 910 and lower tab 920, which may extend radially and outwardly from upper portion 880 and lower portion 890, respectively. Together, upper tab 910 and lower tab 920 may be configured to form a clamp that grips rod 850. In this manner, offset rod connection assembly 820 may retain rod 850 and secure it with respect to shaft 810.

Orthopedic fixation device 800 further may comprise locking cap assembly 830 in some embodiments. In accordance with present embodiments, rotation of locking cap assembly 830 may be used to lock the offset rod connection assembly 820, thus securing rod 850 and preventing further rotation of ball 870. For example, locking cap assembly 830 may be rotated, thus moving the locking cap assembly 830 downward to force upper portion 880 and lower portion 890 together. In this manner, upper tab 910 and lower tab 920 can be clamped onto rod 850 or an artificial facet, for example. In addition, downward movement of locking cap assembly 830 should also secure ball 870 from further rotation, thus locking the angle of rod 850 with respect to shaft 810.

While it is apparent that the invention disclosed herein is well calculated to fulfill the objects stated above, it will be appreciated that numerous modifications and embodiments may be devised by those skilled in the art. Although individual embodiments are discussed herein, the invention covers all combinations of all those embodiments.

What is claimed is:

1. A system for treating a spinal irregularity, comprising:
a bone fastener;
a first coupling rod and a second coupling rod; and
a first derotation apparatus including:
a tube assembly having a longitudinal axis and comprising an inner sleeve and an outer sleeve disposed over the inner sleeve, wherein the inner sleeve includes a distal end for attachment to the bone fastener;
a handle assembly; and
a coupling rod engagement assembly disposed between the tube assembly and the handle assembly, wherein the coupling rod engagement assembly includes a first clamp for attaching to the first coupling rod and a second clamp for attaching to the second coupling rod,
wherein the first clamp is capable of rotating with respect to the longitudinal axis and is capable of rotating with respect to an axis that is perpendicular to the longitudinal axis,
wherein the second clamp is capable of rotating with respect to the longitudinal axis and is capable of rotating with respect to an axis that is perpendicular to the longitudinal axis, and
wherein the first clamp articulates independently of the second clamp.

2. The system of claim 1, wherein the outer sleeve is capable of sliding down onto a distal end of the inner sleeve to engage the inner sleeve and clamp a distal end of the bone fastener.

3. The system of claim 1, wherein the first derotation apparatus includes a locking mechanism capable of securing the tube assembly on the bone fastener, the locking mechanism extending radially from the inner sleeve and comprising a stop, an actuator, and a guide extending between the stop and the actuator.

4. The system of claim 3:
wherein the outer sleeve includes a first opening, a second opening located closer to a proximal end of the outer sleeve than the first opening, and a channel connecting the first opening and the second opening;
wherein the locking mechanism is configured to extend through a first opening in the outer sleeve with the stop engaging the outer sleeve, when the tube assembly is in an unlocked position; and
wherein the locking mechanism is configured to extend through a second opening, with the stop engaging the outer sleeve, when the tube assembly is in a locked position.

5. The system of claim 1, wherein the coupling rod engagement assembly includes a first ball joint comprising an upper portion and a lower portion that match together to form a rotatable ball, the upper portion including a radially extending upper tab, the lower portion including a radially extending lower tab, and the upper tab and the lower tab forming the first clamp for receiving the first connecting rod.

6. The system of claim 5, wherein the ball joint is a spring-loaded ball joint that includes:
an outer washer having a serrated surface, wherein the serrated surface is configured to prevent rotation of the ball by engaging an outer surface of the ball when the ball joint is in a locked position; and
an inner washer fit within the outer washer and having a protruding rim with a smooth surface, and wherein the protruding rim is configured to extend through the outer washer to engage smooth surface to extend through the outer washer engage an outer surface of the ball without preventing rotation of the ball when the ball joint is in an unlocked position.

7. The system of claim 5, wherein the handle assembly includes a handle, and wherein the clamp is configured to close down onto the coupling rod upon tightening of the handle onto the ball joint assembly.

8. The system of claim 1, further comprising:
a second derotation apparatus including:
a second tube assembly comprising an inner sleeve and an outer sleeve disposed over the inner sleeve, wherein the inner sleeve has a distal end for attachment to a second screw;
a second handle assembly; and
a second coupling rod engagement assembly disposed between the tube assembly and the handle assembly, wherein the coupling rod engagement assembly includes a third clamp for attaching to the first coupling rod and a fourth clamp for attaching to the second coupling rod.

9. The system of claim 8, further comprising:
a third derotation apparatus including:
a third tube assembly comprising an inner sleeve and an outer sleeve disposed over the inner sleeve, wherein the inner sleeve has a distal end for attachment to a third screw;
a third handle assembly; and
a third coupling rod engagement assembly disposed between the tube assembly and the handle assembly, wherein the coupling rod engagement assembly includes a fifth clamp for attaching to the first coupling rod and a sixth clamp for attaching to the second coupling rod.

10. The system of claim 1, wherein the bone fastener is a pedicle screw.

11. A system for treating a spinal irregularity, comprising:
a first derotation apparatus including:
a tube assembly having a longitudinal axis and comprising an inner sleeve and an outer sleeve disposed over the inner sleeve, wherein the inner sleeve includes a distal end for attachment to a bone fastener;
a handle assembly; and
a coupling rod engagement assembly disposed between the tube assembly and the handle assembly, wherein the coupling rod engagement assembly includes a first clamp for attaching to a first coupling rod and a second clamp for attaching to a second coupling rod,
wherein the first clamp is capable of rotating with respect to the longitudinal axis and is capable of rotating with respect to an axis that is perpendicular to the longitudinal axis, and
wherein the second clamp is capable of rotating with respect to the longitudinal axis and is capable of rotating with respect to an axis that is perpendicular to the longitudinal axis.

12. The system of claim 11, wherein the outer sleeve is capable of sliding down onto a distal end of the inner sleeve to engage the inner sleeve and clamp a distal end of the bone fastener.

13. The system of claim 11, wherein the first derotation apparatus includes a locking mechanism capable of securing the tube assembly on the bone fastener, the locking mechanism extending radially from the inner sleeve and comprising a stop, an actuator, and a guide extending between the stop and the actuator.

14. The system of claim 13:
wherein the outer sleeve includes a first opening, a second opening located closer to a proximal end of the outer sleeve than the first opening, and a channel connecting the first opening and the second opening;
wherein the locking mechanism is configured to extend through a first opening in the outer sleeve with the stop engaging the outer sleeve, when the tube assembly is in an unlocked position; and
wherein the locking mechanism is configured to extend through a second opening, with the stop engaging the outer sleeve, when the tube assembly is in a locked position.

15. The system of claim 11, wherein the coupling rod engagement assembly includes a first ball joint comprising an upper portion and a lower portion that match together to form a rotatable ball, the upper portion including a radially extending upper tab, the lower portion including a radially extending lower tab, and the upper tab and the lower tab forming the first clamp for receiving the first connecting rod.

16. The system of claim 15, wherein the ball joint is a spring-loaded ball joint that includes:
an outer washer having a serrated surface, wherein the serrated surface is configured to prevent rotation of the ball by engaging an outer surface of the ball when the ball joint is in a locked position; and
an inner washer fit within the outer washer and having a protruding rim with a smooth surface, and wherein the protruding rim is configured to extend through the outer washer to engage smooth surface to extend through the outer washer engage an outer surface of the ball without preventing rotation of the ball when the ball joint is in an unlocked position.

17. The system of claim 15, wherein the handle assembly includes a handle, and wherein the clamp is configured to close down onto the coupling rod upon tightening of the handle onto the ball joint assembly.

18. The system of claim 11, further comprising:
a second derotation apparatus including:
a second tube assembly comprising an inner sleeve and an outer sleeve disposed over the inner sleeve, wherein the inner sleeve has a distal end for attachment to a second screw;
a second handle assembly; and
a second coupling rod engagement assembly disposed between the tube assembly and the handle assembly, wherein the coupling rod engagement assembly includes a third clamp for attaching to the first coupling rod and a fourth clamp for attaching to the second coupling rod.

19. The system of claim 18, further comprising:
a third derotation apparatus including:
a third tube assembly comprising an inner sleeve and an outer sleeve disposed over the inner sleeve, wherein the inner sleeve has a distal end for attachment to a third screw;
a third handle assembly; and
a third coupling rod engagement assembly disposed between the tube assembly and the handle assembly, wherein the coupling rod engagement assembly includes a fifth clamp for attaching to the first coupling rod and a sixth clamp for attaching to the second coupling rod.

20. The system of claim 11, wherein the bone fastener is a pedicle screw.

\* \* \* \* \*